US009713450B2

(12) United States Patent
Claus et al.

(10) Patent No.: US 9,713,450 B2
(45) Date of Patent: Jul. 25, 2017

(54) ITERATIVE RECONSTRUCTION OF PROJECTION DATA

(71) Applicant: GENERAL ELECTRIC COMPANY, Schenectady, NY (US)

(72) Inventors: Bernhard Erich Hermann Claus, Niskayuna, NY (US); David Allen Langan, Clifton Park, NY (US); Omar Al Assad, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 150 days.

(21) Appl. No.: 14/571,086

(22) Filed: Dec. 15, 2014

(65) Prior Publication Data
US 2016/0171723 A1 Jun. 16, 2016

(51) Int. Cl.
G06T 7/00 (2017.01)
A61B 6/03 (2006.01)
G06T 11/00 (2006.01)
A61B 6/00 (2006.01)

(52) U.S. Cl.
CPC .......... *A61B 6/032* (2013.01); *A61B 6/5205* (2013.01); *G06T 11/006* (2013.01); *A61B 6/4441* (2013.01); *A61B 6/481* (2013.01); *A61B 6/487* (2013.01); *A61B 6/504* (2013.01); *G06T 2211/424* (2013.01)

(58) Field of Classification Search
None
See application file for complete search history.

(56) References Cited

U.S. PATENT DOCUMENTS

| 6,768,782 B1 * | 7/2004 | Hsieh | A61B 6/032 378/4 |
| 7,218,702 B2 | 5/2007 | Mistretta et al. | |
| 7,885,371 B2 * | 2/2011 | Thibault | G06T 11/006 378/4 |
| 7,983,462 B2 * | 7/2011 | Sauer | G06T 5/50 382/131 |
| 8,013,307 B2 * | 9/2011 | Ye | G01T 1/1615 250/363.04 |
| 8,503,750 B2 | 8/2013 | Benson et al. | |
| 8,770,838 B2 | 7/2014 | Papaioannou | |
| 8,817,947 B2 | 8/2014 | Vedantham et al. | |

(Continued)

OTHER PUBLICATIONS

Nett, Brian E., et al, "Circular tomosynthesis implemented with a clinical interventional flat-panel based C-arm: initial performance study", Proc. SPIE 6510, Medical Imaging 2007: Physics of Medical Imaging, pp. 1-12, Mar. 17, 2007.

(Continued)

*Primary Examiner* — Kim Vu
*Assistant Examiner* — Molly Delaney
(74) *Attorney, Agent, or Firm* — Pabitra K. Chakrabarti

(57) ABSTRACT

The present disclosure relates to the iterative reconstruction of projection data. In certain embodiments, the iterative reconstruction is a multi-stage iterative reconstruction in which different feature are selectively emphasized at different stages. Selective emphasis at different stages may be accomplished by differentially handling two or more decompositions of an input image at certain iterations and/or by differently processing certain features with respect to each stage.

20 Claims, 5 Drawing Sheets

(56) References Cited

U.S. PATENT DOCUMENTS

| | | | |
|---|---|---|---|
| 2011/0081071 A1* | 4/2011 | Benson | G06T 11/005 |
| | | | 382/154 |
| 2012/0020448 A1* | 1/2012 | Khare | G06T 11/006 |
| | | | 378/4 |
| 2012/0155730 A1* | 6/2012 | Metaxas | G01R 33/5608 |
| | | | 382/131 |
| 2013/0010917 A1* | 1/2013 | Thibault | G06T 11/006 |
| | | | 378/4 |
| 2014/0037049 A1 | 2/2014 | Langan et al. | |
| 2014/0073913 A1 | 3/2014 | Defreitas et al. | |
| 2014/0153690 A1 | 6/2014 | Claus et al. | |

OTHER PUBLICATIONS

Siewerdsen, J.H., et al., "Multi-Mode C-Arm Fluoroscopy, Tomosynthesis, and Cone-Beam CT for Image-Guided Interventions:From Proof of Principle to Patient Protocols", Medical Imaging 2007: Physics of Medical Imaging, pp. 1-11, vol. 6510, 2007.

Godfrey, Devon J., et al., "The effect of averaging adjacent planes for artifact reduction in matrix inversion tomosynthesis", Med. Physics, vol. 40, Issue 2, pp. 1-20, Feb. 2013.

U.S. Appl. No. 14/570,988, filed Dec. 15, 2014, Langan et al.
U.S. Appl. No. 14/602,051, filed Jan. 21, 2015, Langan et al.
U.S. Appl. No. 14/819,192, filed Aug. 5, 2015, Langan et al.
U.S. Appl. No. 14/192,466, filed Feb. 27, 2014, AlAssad et al.
U.S. Appl. No. 14/448,842, filed Jul. 31, 2014, Langan et al.

* cited by examiner

ITERATIVE RECONSTRUCTION OF PROJECTION DATA

BACKGROUND

The subject matter disclosed herein relates to imaging techniques for use in an image-guided procedure, such as to provide accurate imaging of small, high-contrast structures, including contrast-enhanced vasculature and devices.

Various medical procedures involve the intra-arterial injection of contrast agents to visualize vascular structure, and/or insertion and navigation of a tool within a patient's body. For example, needle-based procedures (e.g., lung biopsy, vertebroplasty, RF ablation of liver tumors, and so forth) may involve the insertion and navigation of a needle or needle associated tool through the body of a patient. Such procedures, therefore, benefit from the acquisition of image data suitable for discerning and displaying small structures within the patient body. For example, such image data may be used to evaluate shape and location of vessels feeding a tumor, safely guide a device to the target while avoiding critical structures (e.g., arteries and veins) and obstructions (e.g., bones).

Such image data may be acquired using various types of imaging modalities that employ various radiological principles. For example, technologies such as X-ray fluoroscopy, cone beam computed tomography (CBCT), X-ray computed tomography (CT), and tomosynthesis use various physical principles, such as the varying transmission of X-rays through a target volume, to acquire projection data and to construct images (e.g., three-dimensional, volumetric representations of the interior of the human body or of other imaged structures).

Such conventional modalities, however, may be bulky and may limit the movements and operations performed by a clinician and/or maybe limit aspects of the imaging operation such as the timing and/or administration of contrast agents, to particular conditions. For example, CBCT and CT may employ imager configurations that spin a source and detector about the patient, which may prohibit certain operations being performed near the patient during imaging and may be bulky in implementation. Conversely however, modalities that are less bulky or more flexible in terms of imaging constraints typically operate with a narrower range of viewing angles, and may not provide sufficient image quality for clinical purposes. It may, therefore, be desirable to generate image data suitable for providing 3D volumes with sufficient image quality for the clinical task at hand during a procedure and using a system that is flexible in terms of operator movement and imaging operations.

BRIEF DESCRIPTION

In one embodiment, an iterative image reconstruction method is provided. In accordance with this method, a set of projection images is accessed. A first stage of a multi-stage iterative reconstruction of the set of projection images is performed, each stage comprising one or more iterative steps. The first stage selectively emphasizes a subset of features of the projection images for iterative processing. The selective emphasis of the first stage is defined by one or more parameters specified for the first stage. Subsequent to the first stage, at least a second stage of the multi-stage iterative reconstruction is performed. The second stage selectively emphasizes a different subset of features of the projection images for iterative processing. The selective emphasis of the second stage is defined by one or more parameters specified for the second stage that differ in value or range from the first stage. Upon satisfying a completion criterion, the multi-stage iterative reconstruction is concluded and a final image is generated.

In another embodiment, an iterative image reconstruction method is provided. In accordance with this method, a set of projection images is accessed. An iterative reconstruction comprising two or more stages, each stage comprising a plurality of iterative steps, is performed. At least one stage of the iterative reconstruction selectively emphasizes, relative to other stages, a subset of features of the projection images for iterative processing by applying one or more of selective weighting, thresholding, or clipping based on parameters specified for the respective stage. Upon satisfying a completion criterion, the multi-stage iterative reconstruction is concluded and a final image is generated.

In a further embodiment, an image reconstruction system is provided. The system includes: a display, a memory or storage component storing one or more routines, and a processing component configured to execute the one or more routines. The one or more routines, when executed by the processing component, cause acts to be performed including: accessing a set of projection images; performing a first stage of a multi-stage iterative reconstruction of the set of projection images, each stage comprising one or more iterative steps, wherein the first stage selectively emphasizes a subset of features of the projection images for iterative processing, wherein the selective emphasis of the first stage is defined by one or more parameters specified for the first stage; subsequent to the first stage, performing at least a second stage of the multi-stage iterative reconstruction, wherein the second stage selectively emphasizes a different subset of features of the projection images for iterative processing, wherein the selective emphasis of the second stage is defined by one or more parameters specified for the second stage that differ in value or range from the first stage; and upon satisfying a completion criterion, concluding the multi-stage iterative reconstruction and generating a final image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
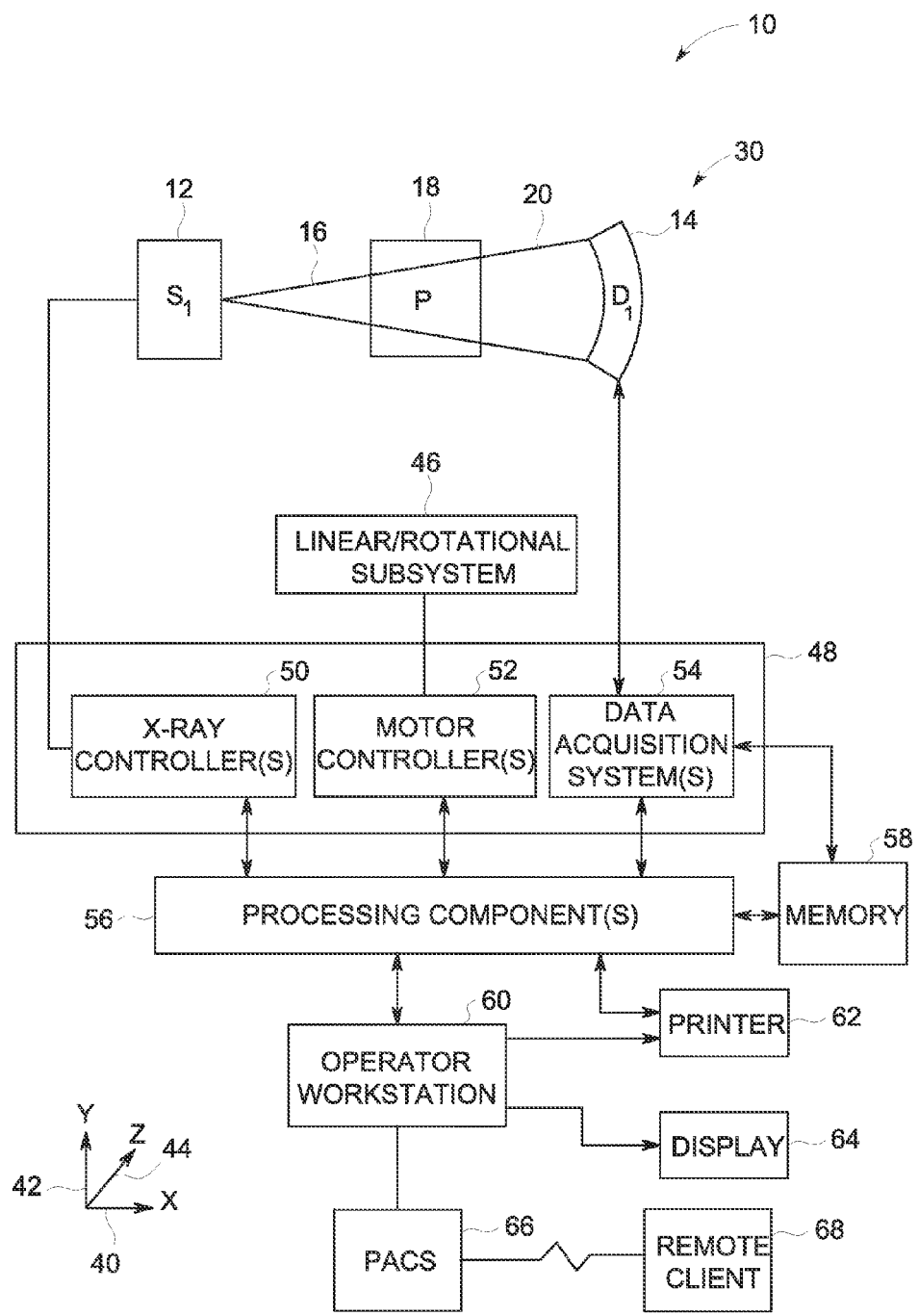
FIG. 1 is a diagrammatical view of an imaging system for use in producing images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

In certain 3D imaging procedures (including procedures using an interventional C-arm or similar system), it is useful to be able to visualize the internal structures of a patient as part of the procedure. Aspects of the present approach utilize C-arm tomosynthesis to provide such images. As discussed herein, in certain embodiments, a C-arm mounted X-ray detector and source (e.g., an X-ray tube) continuously orbit within respective planes above and below the patient support table. In such an embodiment, the operator is provided good access to the patient, in contrast to other types of imaging modalities.

As may be appreciated, in such tomosynthesis acquisitions an acquisition motion or trajectory may be employed having a small tomographic angle. This may be desirable to the extent it allows 3D imaging in situations where cone beam computed tomography (CBCT) and computer tomography (CT) are infeasible due to collision hazards with procedure room apparatus, patient, and/or medical staff (e.g., space and geometric constraints).

However, a consequence of the limited angular range of such an acquisition is that the acquired data set (i.e., the acquired projection images) is considered incomplete (due to the limited angle from which projections are acquired) and the reconstructed volume often possesses many artifacts limiting its clinical value. As discussed herein, reconstruction approaches are described which address reconstruction of such limited angular range projection data sets and which enable three-dimensional (3D) imaging for uses that include, but are not limited to, imaging of vasculature and devices for interventional planning, guidance, and assessment applications. In particular, as discussed herein, the present reconstruction approaches selectively emphasize certain aspects (such as features corresponding to different image scales or frequency bands) of the projection or image data during iterations of a reconstruction process. In this manner, during a multi-stage reconstruction process, different image features may be refined or emphasized during a given stage while other features (e.g., artifacts or noise) may be deemphasized or removed. As discussed herein, such an approach is suitable for reconstructing small structures, such as vasculature and devices, with reduced, minimal, or no blurring. Due to this approach, the reconstruction of the background (e.g., the anatomy surrounding these small structures) is also minimally impacted by artifacts due to out-of-plane structures, as are common with conventional reconstruction algorithms.

With the preceding comments in mind, it should be appreciated that, though C-arm tomosynthesis and limited angular range projection sets are described herein as examples, such embodiments are merely described to facilitate explanation and to provide a working example. It should be appreciated that aspects of the present approach, such as those related to multi-scale reconstruction, may be applicable to other imaging modalities and acquisition approaches. Thus, such examples should be understood to be non-limiting and provided only to simplify explanation by providing an example of one implementation.

In accordance with aspects of the present disclosure, an example of an iterative reconstruction process is described which employs a hierarchical, multi-stage reconstruction approach, such as a hierarchy where the image detail is selectively emphasized in early stages of reconstruction process, and reconstruction of the image background is emphasized in later stages of the reconstruction. During such an iterative process, the parameters that control weighting and processing of the projection images and image update may evolve or change (such as between different discrete stages of the reconstruction) so as to emphasize different characteristics or features during different stages of the reconstruction process. The specific characteristics of the algorithm therefore change throughout the sequence of iterations, depending on the desired performance characteristics at each stage.

By way of example, in one implementation the reconstruction approach is parameterized to hierarchically improve or optimize the resolution of vasculature and devices (i.e., small, high-contrast objects) in image data. In such an embodiment, the imaged volume may be considered to include small, high-contrast objects in a low contrast background. In one implementation, the reconstruction incorporates one or more of: (1) a re-weighting of image information at different image scales and/or frequency bands (i.e., selective emphasis of feature at different image scales or frequency bands); (2) a thresholding step in the image domain (i.e., in the 3D volume domain) in order to combat streaks and out-of-plane artifacts; and (3) a thresholding and/or clipping step on the projection data before the back-projection, in order to make the artifact management in the backprojection step most effective. Depending on the embodiment, these operations may be combined in different ways and/or at different stages of the iterative algorithm to improve image quality of the reconstructed tomosynthesis volumes.

With the preceding in mind, an example of a single-plane tomosynthesis imaging system 10 suitable for acquiring X-ray attenuation data for reconstruction as discussed herein is provided in FIG. 1. As discussed herein, in certain implementations the tomosynthesis acquisition operates such that the X-ray detector and source (e.g., an X-ray tube) orbit one or more times above and below the patient. For example, the source and detector may each orbit within separate respective planes or other constrained 2D or 3D trajectories, one above and one below, the patient. In one such implementation, the orbit may have a half tomo angle of 15° to 30° and an orbit period of 3 to 8 seconds. Relative to other imaging modalities (e.g., CBCT and computed tomography (CT)), the tomosynthesis acquisition gantry motion has a significantly reduced footprint, providing the opportunity to perform a tomosynthesis acquisition in circumstances where other imaging approaches are prohibited due to collision with procedure room apparatus, the patient, and/or staff. A continuous orbit, when employed, provides timing flexibility for the procedure and imaging operation, enabling manual injection, physiologic gating, selection of the bolus delay to be reconstructed, and so forth. The present approach, however, does not require continuous or continued orbital motion of the source and detector during the procedure and may be used when as little as a single orbit (or even a fraction of, or a subset of projection images from a single orbit) of projection image data is acquired.

In the embodiment illustrated in FIG. 1, imaging system 10 includes a source of X-ray radiation 12 and a detector 14. The X-ray source 12 may be an X-ray tube, a distributed X-ray source (such as a solid-state or thermionic X-ray source) or any other source of X-ray radiation suitable for the acquisition of medical or other images. The X-rays 16 generated by the source 12 pass into a region in which a patient 18, is positioned during a procedure. In the depicted example, the X-rays 16 are collimated to be a cone-shaped beam, e.g., a cone-beam, which passes through the imaged volume. A portion of the X-ray radiation 20 passes through or around the patient 18 (or other subject of interest) and impacts a detector array, represented generally as the detector 14. Detector elements of the detector 14 produce electrical signals that represent the intensity of the incident X-rays 20. These signals are acquired and processed, as discussed herein, to reconstruct images of the features within the patient 18. While FIG. 1 depicts a single-plane imaging system 10, in certain embodiments the imaging system may be a bi-plane imaging system that includes a an additional source of X-ray radiation and an additional detector configured to acquire projection images at a different direction, location, and/or timing than the source 12 and detector 14.

In the present example, the source 12 and detector 14 may be a part of an imager subsystem 30. As depicted, the imager 30 positions the source 12 and the detector 14, at rest, generally along a direction, which may correspond to the AP direction of the patient 18 in certain embodiments. For example, the imager 30 may acquire X-ray images or X-ray projection data over a limited angular range with respect to one side or facing (e.g., the anterior/posterior (AP) direction) of the patient 18, thereby defining data in a first plane (e.g., a frontal plane of the patient 18). In this context, an imaging plane may be defined as a set of projection directions that are located within a certain angular range relative to a reference direction. For example, the frontal imaging plane may be used to describe projection views within an angular range that is within, for example, 60 degrees of the PA (posterior/anterior) direction of the patient. Similarly, the lateral imaging plane, if imaged by the imager 30 or a second imager, may be described as the set of projection directions within an angular range that is within 60 degrees of the lateral/horizontal left/right projection direction.

In accordance with present embodiments, the imager 30 may be moved relative to the patient or imaged object along one or more axes during an examination procedure during which projection data is acquired. For example, the imager 30 may move about a first axis of rotation 40, a second axis of rotation 42, or a third axis of rotation 44, or any combination thereof. In one embodiment, the translation and rotation of the imager 30 may be determined or coordinated in accordance with a specified protocol.

The movement of the imager 30 may be initiated and/or controlled by one or more linear/rotational subsystems 46. The linear/rotational subsystems 46, as discussed in further detail below, may include support structures, motors, gears, bearings, and the like, that enable the rotational and/or translational movement of the imager 30. In one embodiment, the linear/rotational subsystems 46 may include a structural apparatus (e.g., a C-arm apparatus having rotational movement about at least two axes) supporting the source and detector 12, 14.

A system controller 48 may govern the linear/rotational subsystems 46 that initiate and/or control the movement of the imager 30. In practice, the system controller 48 may incorporate one or more processing devices that include or communicate with tangible, non-transitory, machine readable media collectively storing instructions executable by the one or more processors to perform the operations described herein. The system controller 48 may also include features that control the timing of the activation of the sources 12, for example, to control the acquisition of X-ray attenuation data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imager. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the imager 30 and the linear/rotational subsystems 46. In the illustrated embodiment, the circuitry may include an X-ray controller 50 configured to operate the X-ray source 12 so as to time the operations of the source and to interleave the acquisition of X-ray attenuation data when needed. Circuitry of the system controller 48 may also include one or more motor controllers 52. The motor controllers 52 may control the activation of various components that are responsible for moving the source 12 and the detector 14. In other words, the motor controllers may implement a particular trajectory for the imagers 30.

The system controller 48 is also illustrated as including one or more data acquisition systems 54. Generally, the detector 14 may be coupled to the system controller 48, and more particularly to the data acquisition systems 54. The data acquisition systems 54 may receive data collected by read out electronics of the detector 14 and in certain embodiments may process the data (e.g., by converting analog to digital signals or to perform other filtering, transformation, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform the image acquisition and reconstruction techniques described herein. Further, the processing components 56 and the memory components 58 may coordinate in order to perform various image reconstruction processes.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared throughout the imaging facility and may also be shared with other facilities, for example, a remote client 68. The remote client 68 may include hospitals, doctors' offices, or any other similar client.

Figure 2:
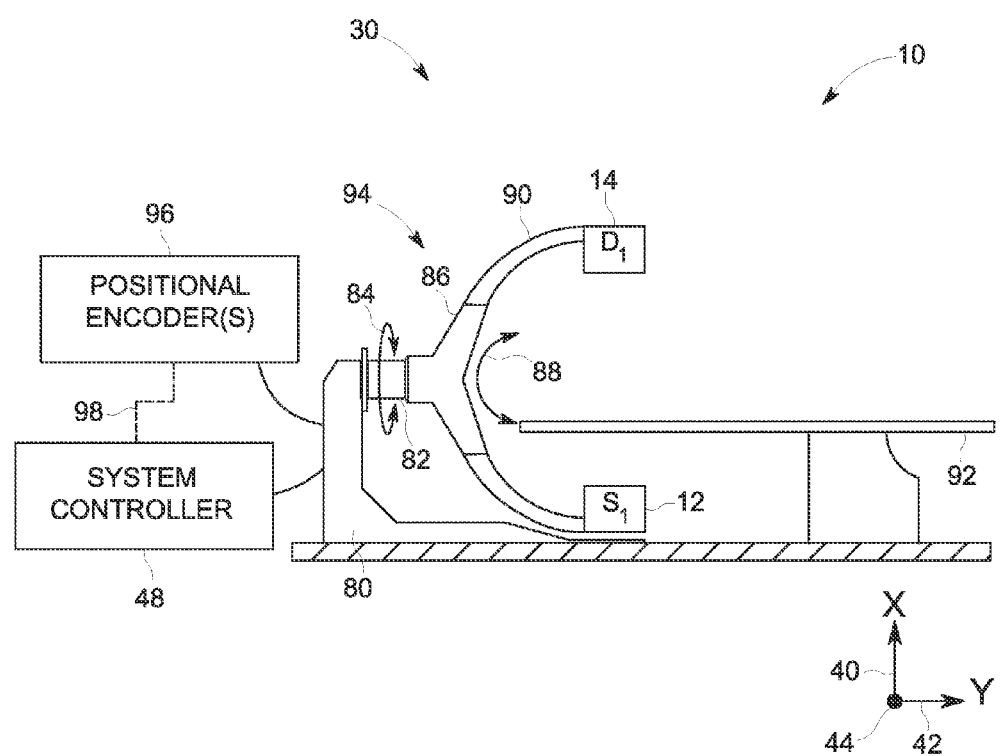
FIG. 2 is a schematic side view of an imaging system in which an imaging apparatus obtains projection data along a plane via rotation about two axes, in accordance with aspects of the present disclosure.

Various aspects of the present approaches may be further appreciated with respect to FIG. 2, which is a side view of an embodiment of the system 10. The imager 30, as illustrated, includes a base 80 and a rotatable extension 82 extending from the base 80. In the illustrated embodiment, the base 80 is a floor-mounted base such that the imager 30 may be secured to a floor of an imaging area in which it is positioned. In other embodiments, however, the base 80 may be secured to other surfaces (e.g., a wall or ceiling) and/or may be mobile or movable.

The rotatable extension 82 is depicted as extending generally along the second axis of rotation 42, and enables the source 12 and the detector 14 to move about the second axis of rotation 42. For example, the rotatable extension 82 may enable the source 12 and the detector 14 to move about the second axis of rotation 42 in a manner that maintains their position relative to one another throughout the movement. The rotation enabled by the rotatable extension 82 is shown as double-headed arrow 84. The rotatable extension 82 is coupled to a moving structure 86 (e.g., directly or indirectly via an extension arm), which enables the source 12 and the detector 14 to move about the third axis of rotation 44. This rotation about the third axis of rotation 44 is depicted as double-headed arrow 88.

The moving structure 86 may be a geared or track structure that is motively coupled to a support structure 90 that physically supports the source 12 and the detector 14, and may be in the form of a C-arm, or any other shape that positions the source 12 and the detector 14 on either side of the patient 18. As illustrated, the support structure 90 includes an arcuate structure that extends from a first side of a patient table 92, around the patient table 92, and to a second side of the patient table 92. In this way, the source 12 and the detector 14 generally remain positioned at opposite ends and/or on opposite sides of the patient (not shown) positioned on patient table 92. Together, the base 80, the rotatable extension 82, the moving structure 86, and the support structure 90 may be considered to be the structure 94 of the imager 30.

The imager 30 may include various motors, actuators, or other features responsible for movement of the various structures of the imager 30, and they may be communicatively coupled to one or more positional encoders 96. The one or more positional encoders 96 may encode the respective positions of any one or more components of the imager 30 in a manner that facilitates processing by the system controller 48. In such an implementation, the positional encoders 96 may provide feedback 98 (for example via wired or wireless signals) to the system controller 48. The system controller 48 may use this feedback 98 to control the imager 30.

As an example, the system controller 48 may simultaneously move the source 12 and the detector 14 together about the first axis of rotation 40, the second axis of rotation 42, or the third axis of rotation 44, or any combination thereof, and obtain X-ray attenuation data for a subset of the traversed view angles. In one embodiment, the system controller 48 may receive positional information from the positional encoders 96 relating to the imager 30 and may calculate a trajectory (or update a modeled trajectory) for either or for both of the source and detector 12, 14 using this positional feedback information.

Furthermore, the system controller 48 may synthesize one or more volumetric images using data obtained by the imager 30. Tomosynthesis reconstruction algorithms, as discussed herein, may be used to reconstruct a 3D volumetric image of the imaged region of interest. In one such embodiment, the imager 30 may perform an acquisition of data using an acquisition trajectory (e.g., a circular, ellipsoidal, or similar path traced by the source 12 below (or above) the patient 18 and a corresponding circular, ellipsoidal, or similar path traced by the detector above (or below) the patient 18, referred to herein as a frontal tomosynthesis trajectory). An example of such a motion (i.e., an "orbit" as used herein) is conceptually demonstrated in FIG. 3 in the context of imager 30. In this example, the imager 30 may obtain projection data from a plurality of projection directions, but these projection directions may be limited by the angular range of motion of the imager 30 (e.g., the limited angular displacement about the second rotational axis 42) and/or the presence of proximate structures or personnel. In one embodiment, the angular range of the trajectory may also be limited due to temporal constraints. In one example, the angular range of an elliptical orbit that is part of the trajectory may be defined by the requirement that the orbit may have to be traversed in a certain amount of time, e.g., in 3 seconds or less.

With the preceding in mind, as used herein, a tomosynthesis trajectory of an imager may be described as a path (e.g., a line, curve, circle, oval, and so forth, as well as combinations thereof) traced by an X-ray source during image acquisition. A tomosynthesis acquisition by an imager or imager subsystem occurs over a limited angular range with respect to the patient (such as with respect to one side, e.g., the front, back, left side, or right side, of the patient), and thus a trajectory will typically move the source within this limited angular range with respect to the imaged subject.

As noted above, and as shown in FIG. 3, the motion of the gantry during the tomosynthesis data acquisition may be referred to as a trajectory or as an orbit. For example, an X-ray source may be moved (i.e., have a trajectory) in a circular or oval motion (e.g., an orbit) in front of the patient, without rotating around the patient, thereby acquiring X-ray projection data over a limited angular range with respect to the patient. By way of example, a present implementation relates to the use of a C-arm to perform tomosynthesis imaging in an interventional imaging context. In one such imaging mode, the detector 14 and tube (e.g., source 12) orbit one or more times within respective planes above and below the table 92. In one embodiment, the orbit generally has a half tomosynthesis angle of 15° to 30° and an orbit may be traversed in 3 to 8 seconds. In some embodiments, such trajectories may be periodic in that the path traced by the X-ray source may be repeated throughout the examination. Such a limited-angle motion is in contrast to the spin-type source motion or trajectory typically associated with cone beam computed tomography (CBCT) and computed tomography (CT) type systems and acquisitions.

Figure 3:
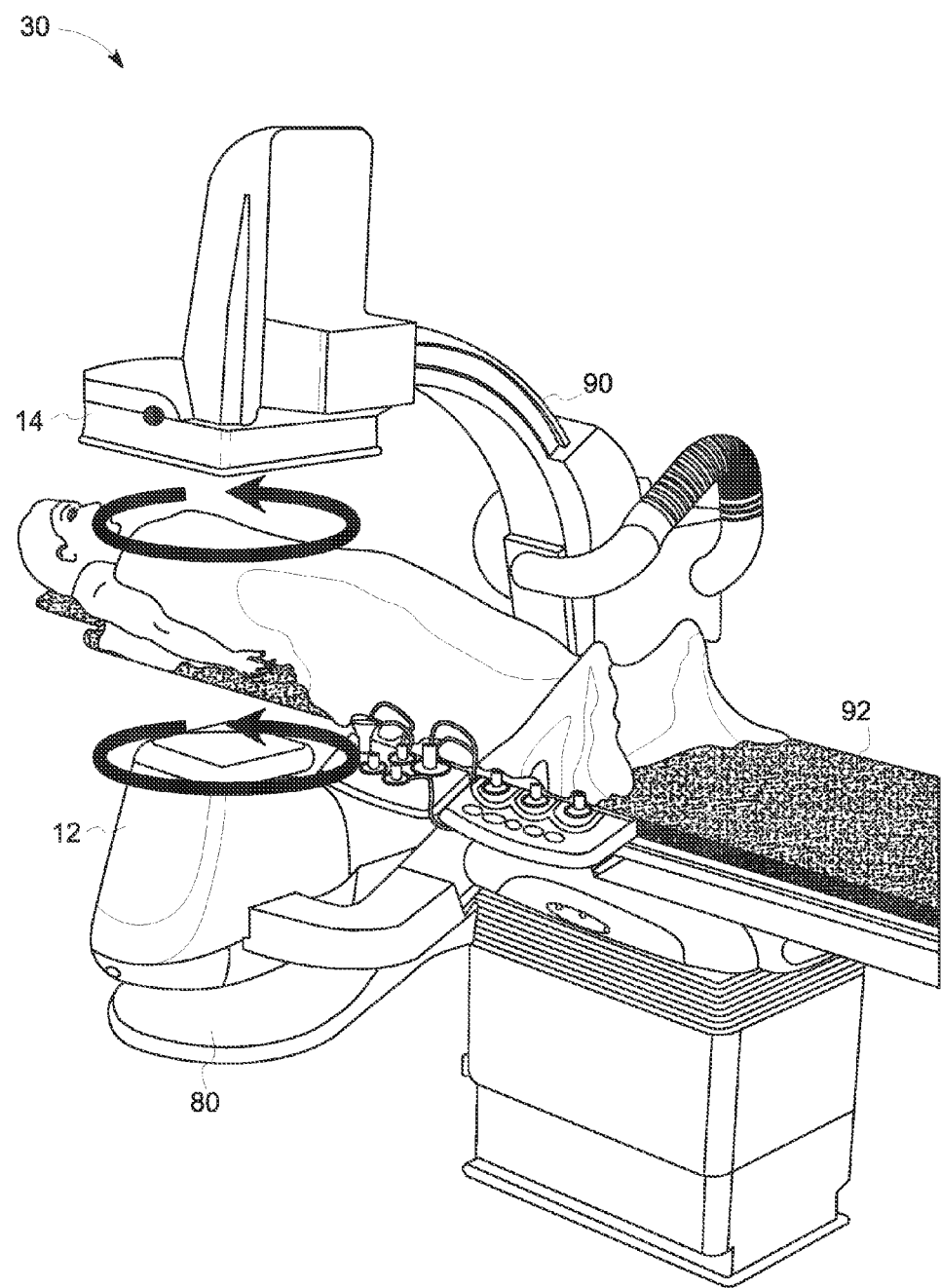
FIG. 3 depicts movement of a source and detector of a C-arm tomosynthesis system in accordance with aspects of the present disclosure.
Figure 4:
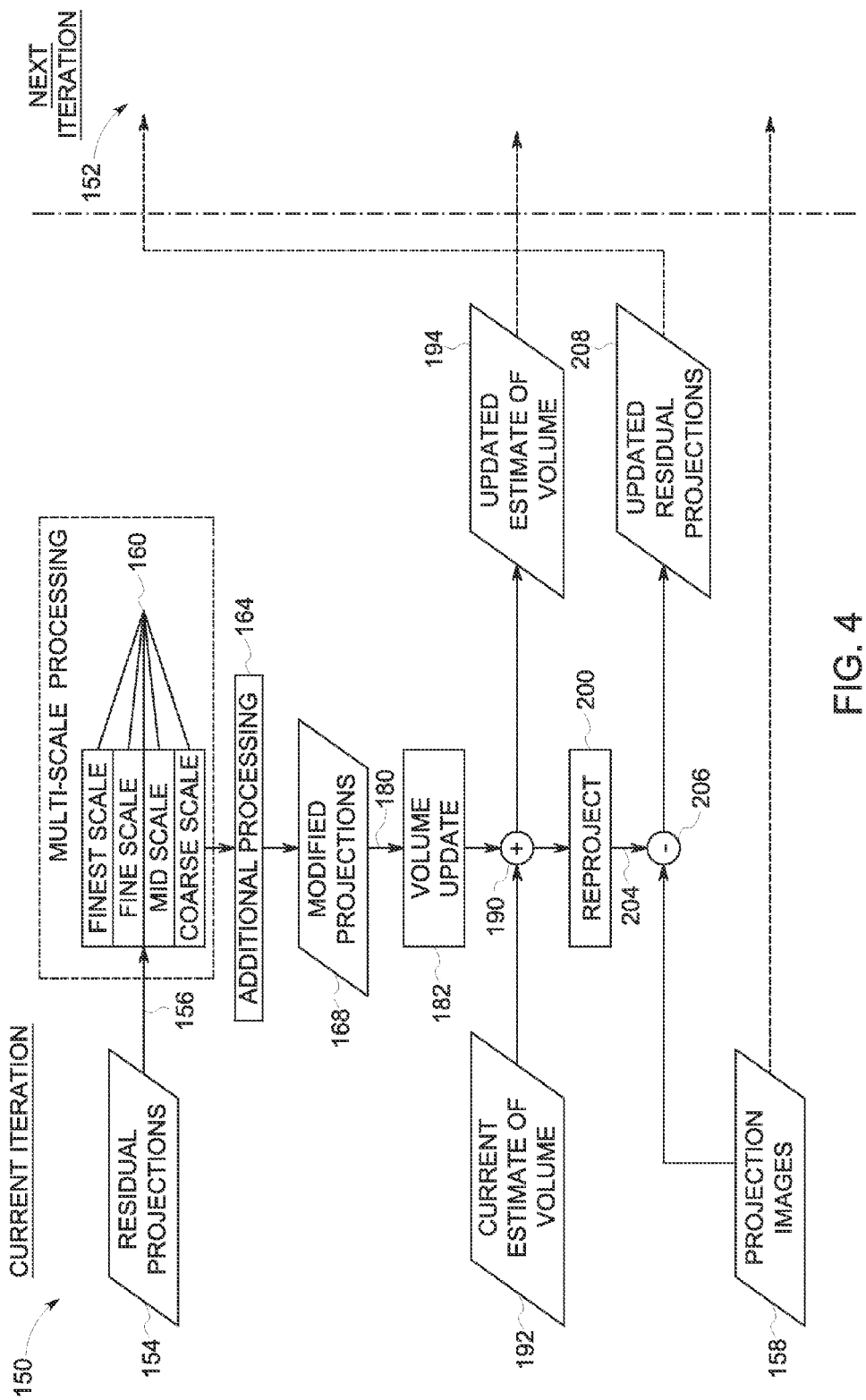
FIG. 4 depicts a process flow for an iterative reconstruction process, in accordance with aspects of the present disclosure.

With the preceding in mind, and turning to FIG. 4, a process flow 120 is depicted showing one iterative update step of a multi-stage reconstruction algorithm suitable for reconstructing projection data, such as projection data acquired over a limited angular range using a system such as shown in FIGS. 1-3. The depicted reconstruction process may be performed during the course of an interventional or other imaging procedure, such as to generate 3D information for planning, guidance, and/or assessment prior to or during the course of the procedure. Intra-procedure uses of 3D information include, but are not limited to: 3D vasculature roadmaps, device guidance, embolization planning and assessment, and device visualization (stents, coils, guide-wires, etc.).

As discussed herein, the present approaches provide improved image quality in tomosynthesis imaging, including reduction of streaks and out-of-plane artifacts. In particular, in conventional approaches a tomosynthesis reconstruction algorithm may utilize some form of filtered backprojection (which is not effective in combating artifacts and/or streaks) or an iterative update with a penalty term (i.e., a "regularizer") that guides toward an expected result or solution, thereby affecting the imaging result based on these expectations, such as enhancing smoothing and so forth. However, in most implementations the backprojection-update step and the penalty-minimization step are alternated, i.e., a streak or out-of-plane artifact is first introduced via the backprojection step, and the penalty term is then applied "after the fact" in order to minimize the impact of out-of-plane structures. Conversely, in certain embodiments of the present approach, streaks are not introduced in the first place, thereby ensuring superior image quality and fidelity.

In particular, in accordance with certain embodiments, a multi-stage, iterative approach for tomosynthesis reconstruction is employed. In such embodiments, the reconstruction process may be broken down into two or more stages, each of which are directed to selectively emphasizing different aspects of image quality or detail (such as selectively emphasizing features or structures corresponding to different image scales or frequency bands). In such an implementation, each stage can, correspondingly, employ different parameters or ranges of parameters (e.g., weights, thresholds, criteria) during that stage of the iterative reconstruction. With this overall multi-stage framework in mind, each iteration step of the reconstruction: (a) creates modified projection images, such as by processing or preparing either the projection data (in an initial iteration) or the residual projection data (as discussed below); (b) backprojects the modified projection images to create an image volume update for the current estimate of the image volume; (c) creates a modified image volume update for the current iteration; (d) adds (or otherwise combines) the modified image volume update to the current image estimate to form an updated estimate of the image volume; (e) re-projects the updated estimate of the image volume; and (f) creates residual projection images for use in the next iteration. The iterated steps may be repeated until a completion criterion is met for a given stage (e.g., a cost function is minimized or an empirically determined number of iterations have been performed (e.g., 10-200 iterations)) before proceeding to the next stage or, if in the final stage, concluding the reconstruction. Since certain implementations of the reconstruction approach as disclosed herein operate in multiple stages, each stage may have its own stopping criterion (e.g., number of iterations).

With respect to the creation of the modified projection images, in certain implementations this may be accomplished by multi-scale or frequency band processing, as discussed herein. Creation of the modified projection images may also involve thresholding and/or clipping of the projection images and/or the application of positivity constraints. Similarly, in certain embodiments, creation of the modified update volume may involve one or more of thresholding, clipping, application of a positivity constraint, constraining to a support region, and/or scaling of the update volume.

With the preceding discussion in mind, and turning to FIG. 4, a more detailed explanation of various implementations is provided. In FIG. 4, a current step 150 of one stage of a multi-stage iterative reconstruction algorithm is depicted. Such a step 150 may be representative of the steps performed in any of the different stages of the overall reconstruction process.

In the depicted implementation, residual projection images 154 initially undergo multi-scale or frequency band processing (e.g., filtering). In the initial iteration, the initial projection images (i.e., the raw projection images 158 after processing to be linear for attenuation or otherwise processed for reconstruction) may be processed in the absence of residual projections 154. This is equivalent to initializing the reconstructed volume to be a volume containing only zeros, and reprojecting, before computing residual projection images. In another embodiment, the volume may be initialized as a uniform volume (maybe constrained to a known or estimated support region). To simplify explanation, the input images, (e.g., residual projections 154) are generally described and discussed herein as conventional or simple images. However, it should be appreciated that the input images to the iterative reconstruction process described herein may be any suitable images, including images derived from or used in additional processing steps, including, but not limited to digital subtraction (e.g., digital subtraction angiography) images.

In certain embodiments, this step consists of a decomposition (step 156) of the projection image (i.e., residual projections 154) into different frequency bands or image scales (e.g., resulting in a set of frequency or scale specific projection images 160). By way of example, in terms of a decomposition into different image scales, a multi-scale decomposition may be employed to generate an arbitrary number (e.g., 2, 3, 4, 5, and so forth) of images each having content corresponding to a specified image scale (e.g., coarse-scale, mid-scale, fine-scale image content). The different frequency bands or image scales of the projection images 160 may undergo different processing or weighting (i.e., each frequency band or image scale may be differently weighted) (i.e., multi-scale processing). After multi-scale processing, the decomposed projection images 160 are reassembled or recombined and may undergo additional processing 164 to generate modified projections 168. In one embodiment, the decomposition, weighting, and recombination are performed within a single filtering step, i.e., a combined filter is constructed reflecting the combined properties of these steps. In one embodiment, this filter consists of a linear combination of multiple Gaussian filters with different size/standard deviation. In another embodiment the filter is created in the Fourier domain.

As will be appreciated, selective emphasis of different image scales or frequency bands (as part of the multi-scale processing or additional processing steps) may be used to approximate various filtering effects. For example, an approximation to a ramp filter may be generated by assigning larger and larger weights to finer and finer image scales. In addition, noise may be managed by assigning a (relatively) smaller weight to the fine(r) image scale(s). In this manner, the impact of noise in the projection data can be reduced. Similarly, selective emphasis and/or weighting of the different frequency bands or image scales may also be used to perform an unsharp-masking operation, such as by suppressing the coarse scale background relative to the fine-scale image content.

Further, it should be appreciated that in different stages and/or in different iterative steps within a stage, different weights and/or thresholds may be employed. That is, processing of the projection image corresponding to a given frequency band or image scale may change over the course of the iterative process. Thus, depending on the stage of the reconstruction, different iterations of the iterative process may apply different weights and/or thresholds in processing the projection images at a given frequency band or image scale. For example, as noted above, in one embodiment the respective weightings or weighting scheme applied to the decomposed images during multi-scale processing differs between different stages of the reconstruction process. In one such example, during one stage of the reconstruction the weightings may remain the same (or may change within a range specified for that stage) as the iteration steps are performed throughout that stage. However, upon completion of that stage of the iterative reconstruction and initiation of the next stage, the weights (or the range in which the weights vary) may change to reflect the different processing priorities of the new stage of the reconstruction process (thus representing a selective emphasis on image features in the new stage that are different from the features that were emphasized in the previous stage). Similarly, the image scales or frequency bands into which the projection images 154 are decomposed may change between different stages of the reconstruction process.

In one current implementation three scales are used, though four scales (as shown in FIG. 4) or more (e.g., five, six, and so forth) or less may also be employed. As noted above, the number of image scales or frequency bands into which projection images 154 are decomposed may differ between stages of the reconstruction process. In one implementation, the decomposed projection images 160, each representing a different frequency band or image scale, may be generated as difference images between different smoothed versions of the projection images, where rotationally symmetric 2D Gaussian smoothing kernels of different size (i.e., standard deviation) are used to generate the smoothed versions of the projection images. As will be appreciated, different smoothing kernels may be applied and, indeed, smoothing kernels and/or multi-scale filtering may be adapted to specific tomosynthesis trajectories. In one embodiment, e.g., when designing the filters in Fourier space, the filter design may not be associated with a discrete number of scales (or frequency bands), but the appropriate behavior may be designed in the continuous frequency scale of Fourier space. In other embodiments, similar processing may be applied using non-linear filters (e.g., gray-scale morphology) or other approaches.

In one embodiment, some or all of the residual projection images output by the multi-scale processing step may undergo additional processing 164. For example, in one embodiment a thresholding operation (e.g., a soft-thresholding operation) may be applied to some or all of the filtered projection images as part of such additional processing 164. In one such embodiment, the soft-thresholding operator may be of the following form:

$$Img_{out}=\max(abs(Img_{in})-\delta,0)*\text{sign}(Img_{in}). \quad (1)$$

That is, this step retains only the part of the signal/pixel value that exceeds a given threshold $\delta$, with the correct sign (negative or positive), while all other values (with absolute value less than $\delta$) are set to zero. In this manner, soft-thresholding serves to suppress small amplitude components of the signal/image (which may include noise), and will thus sparsify the output images. Depending on the implementation, soft-thresholding parameters may be derived from the image data itself (at each iteration), from a prescribed schedule, or, according to a hybrid scheme, based on the image values at certain stages of the iterative process. In one embodiment, hard thresholding may be used. In hard thresholding, all values with absolute value less than $\delta$ are set to zero, while all other values are retained.

In addition, some or all of the filtered images (i.e., the images after the multi-scale or frequency band processing) may undergo a clipping operation as part of additional processing 164. In one embodiment, the clipping operator is of the following form:

$$Img_{out}=\min(abs(Img_{in}),\epsilon)*\text{sign}(Img_{in}). \quad (2)$$

That is, the clipping step retains all parts of the signal/image that are less than a given threshold $\epsilon$. The clipping step therefore serves to equalize the different components of the image and (partially) suppresses large amplitude data points, which may represent "outliers" in the data.

As with the weighting schemes discussed above, thresholding values for one or both the thresholding and clipping operations may change between different stages of the reconstruction process to reflect the differing priorities of the different stages of the iterative reconstruction process. That is, for a given stage of the reconstruction, the thresholds may be specified for each iterative step to certain values or to certain ranges of values, which may differ from the values or ranges of values specified of the iterative steps performed in other stages of the reconstruction process.

Further, depending on the stage of the reconstruction, a positivity constraint may be applied so as to "clip" all negative values, setting them to zero as part of the additional processing 164. This operation may be useful, for example, when the object of a given stage of the reconstruction process is to reconstruct high-attenuation structures (i.e., those structures that are positive with respect to the corresponding background). Such an operation may also help address the introduction of image content that is mainly attributable to overshoot/undershoot characteristics of the frequency-band processing (which in the detail reconstruction stage corresponds to a high-pass, or high-frequency band, filter). In some contexts, a negativity-enforcing operator may also be used (e.g., when reconstructing an object with small, low-attenuation structures embedded in a high-attenuation background).

Thus, to summarize the preceding points, a projection image or images or, after the first iteration of an iterative reconstruction, a residual projection image or images 154 may undergo multi-scale or frequency band processing. For example, a residual projection image or images 154 may be decomposed 156 based on one or both of frequency bands or image scales (e.g., fine, mid, or coarse) to generate a set of decomposed projection images 160 (i.e., one for each frequency band or image scale in the decomposition). Within the multi-scale or frequency band processing step, each decomposed projection image may be processed differently both within an iteration step and between different iteration steps. By way of example, within an iteration step, different image scales or frequency bands of decomposed projection images 160 may be weighted differently (e.g., a given projection image may receive full weighting, a zero weighting, a weighting greater than one (i.e., an overweighting) or any appropriate incremental weighting in between) so as to selectively emphasize certain of the image scale or frequency bands relative to others. As the iterative process proceeds, the respective weights used to process each frequency band or image scale may change or adapt to correspond to changes in emphasis of the reconstruction process at different stages (i.e., initial, mid, and late stage processing). Indeed, in certain embodiments, even the number of decomposition bands or image scales may change. For example, at an initial stage, decomposition may be into four bands or image scales, while at a later stage decomposition may be into a different number of bands or image scales, such as three. As mentioned before, the multi-scale or frequency band processing (i.e., the steps of decomposing, weighting and recombining) may be combined into a single filtering step within an iteration. Similarly, this filtering step may not have discrete image scales or frequency-bands associated with it. After differentially weighting the different decomposition projection images 160, the results of the differential weighting of the different decomposition projection images 160 are recombined. Further processing operations may be performed on the different filtered projection images at step 164. Examples of such operations include, but are not limited to thresholding (e.g., soft thresholding), clipping, and/or imposition of a positivity or negativity constraint. Note that the steps of thresholding and clipping differentially emphasize some structures within a certain contrast range, while suppressing low contrast structures in the image. Turning back to FIG. 4, the filtered images are thus further processed in such an implementation to generate a set of modified projections 168. In one embodiment, these further processing steps 164 (e.g., thresholding, clipping, and/or the positivity constraint) may also be applied within the multi-scale or frequency band processing step, e.g., by applying them to one or more of the decomposed images 160. In one embodiment, these modified projections are backprojected (step 180) to generate a volume update 182 in image space (as opposed to projection space).

As will be appreciated, in an implementation where the projection data is acquired using a tomosynthesis imaging modality, a limited number (i.e., 10, 20, 25, and so forth) of projection images are typically generated at a wide angular spacing relative to one another (this is in contrast to modalities such as CT, where projections are acquired over essentially the entire angular range, with a small angular spacing). As a result of the limited number of projection images and their angular spacing, conventional image reconstruction for tomosynthesis often suffers from streak artifacts through the reconstructed volume due to high-contrast structure within the imaged volume. Specifically, a conventional tomosynthesis reconstruction (e.g., simple backprojection) of a single, small object within the imaged volume will generally lead to bright "streaks" passing through the reconstructed volume, with the streaks intersecting (and constructively adding) at the true location of the object. The streaks (at any location other than the true location of the object) are undesirable artifacts.

With this in mind, in one implementation, a thresholding operation (e.g., a soft-thresholding operation, as discussed above with respect to the processing of the projection images 160) may be performed after the backprojection 180 (i.e., on the backprojected images) to reduce, minimize, or eliminate such streak artifacts in the update volume 128. In particular, after such a soft-thresholding operation the high-contrast structure(s) remains, with the streaks being suppressed. This approach may be most effective when the contrast of the imaged object/structure is generally equal in all projection images 160. As will be appreciated, in addition to soft-thresholding, other image processing operations including, but not limited to, clipping and imposition of a positivity constraint may be applied to the backprojected images used to generate the image volume update 182. Alternatively, other approaches for managing streak artifacts may be used as well. These include hard thresholding, order-statistics based backprojection (where, for example, at each voxel the average backprojected value from all projection is taken, after eliminating the M largest, and the N smallest values), weighted backprojection, and so forth. As with those operations performed on the filtered projection images, thresholding values or other relevant parameters of an iterative step may have values that depend on the stage of the reconstruction process. That is, these value or parameters (or their respective ranges) may differ for different respective stages of the reconstruction.

In addition, in certain embodiments the update image (i.e., image volume update 182) may undergo a scaling operation prior to combination (step 190) with the current volume estimate 192. The scaling of the update image 182, when employed, may speed up convergence of the reconstruction algorithm. In particular, in implementations where a soft-thresholding step is employed to reduce streaks, the soft-thresholding may also, as an unintended consequence, reduce the amplitude of the desirable image detail. In such instances the scaling may be employed to counter-act the contrast reduction.

With respect to the current volume estimate 192 noted above, in an initial step of an iteration the current estimate 192 may be an analytic reconstruction (e.g., a filtered backprojection) of the initial filtered projection images. In another embodiment the initial estimate of the current volume may be set to zero, or to a uniform constant value (e.g., within a known or estimated support region). In subsequent iterations, the current estimate 192 will be the previous updated estimate 194 (i.e., from the preceding iteration), where the preceding updated estimate 194 is obtained by combining 190 (i.e., adding) the image volume update 182 and current image estimate 192 from that iteration.

As shown in FIG. 4, in addition to generating the updated volume estimate 194, the combination of the image volume update 182 and current image volume estimate 192 may be reprojected (step 200) to generate a representation 204 of the updated estimate in projection space (i.e., an update projection image). In the depicted example this projection space representation 204 of the updated volume estimate is subtracted from the projection images 158, to generate the update residual projections 208, which are used as the residual projections 154 in the next iterative step. The initial projection images 158 remain unchanged in the next iterative step (and throughout the iterative reconstruction process).

With the preceding discussion in mind, an example of a stage-specific parameter schedule is provided to facilitate explanation of the present approach. In this example, the various parameters (e.g., weights, thresholds, and so forth) are shown as evolving or changing over the course of an iterative reconstruction process based on the stage of the reconstruction process. In this example four stages of a multi-stage iterative reconstruction, each having a different goal or purpose and correspondingly different parameters, are described for illustrative purposes. As will be appreciated, the stages and corresponding settings described are merely to facilitate explanation by providing an example of an implementation. Therefore the described setting and parameters should be understood in this context as part of an example, and not as limitations to the approach.

In particular, in one described example the envisioned application may be neuro-perfusion imaging. In such applications, conventional tomosynthesis reconstruction approaches are susceptible to out-of-plane blur (e.g., due to out-of-plane high-contrast vessels), which has a significant negative impact on reconstructed image intensity in the background (i.e., the parenchyma). With this in mind, the present example is directed toward reducing or eliminating the impact of these high-contrast structures on the background. Conventionally, there exist two options: first, one can detect and eliminate these structures/vessels in the projection images before reconstructing the volume (e.g., by replacing the pixel values in the corresponding image regions by interpolated values); and second, one can reconstruct the structures/vessels first and then they will "automatically" be removed from the residual images that serve as input for later iteration steps. Note that metal artifact reduction in conventional reconstruction methods typically uses strategies corresponding to the first option, i.e., identifying the metal/high-attenuation structures first (sometimes by reconstructing, segmenting and re-projecting), and then eliminating the metal structures from the projection data by interpolating across those regions, before performing the main reconstruction step. Conversely, the present approach as disclosed herein relies more on the second option.

In the present example, an approach is described that relies mainly on the second of these two options to, first, reconstruct fine-scale detail in the volume (e.g., vessels), and essentially incrementally remove their contribution from the residual projection images 154 that are considered in subsequent iterations as input to the creation of image volume updates 182. Subsequently, in a later stage of the iterative reconstruction, the coarse-scale, low frequency background information is reconstructed. Thus, in this example, over the course of the iterative reconstruction process, emphasis shifts from the fine scale to the coarse scale. A summary of such a schedule is shown in FIG. 5.

Figure 5:
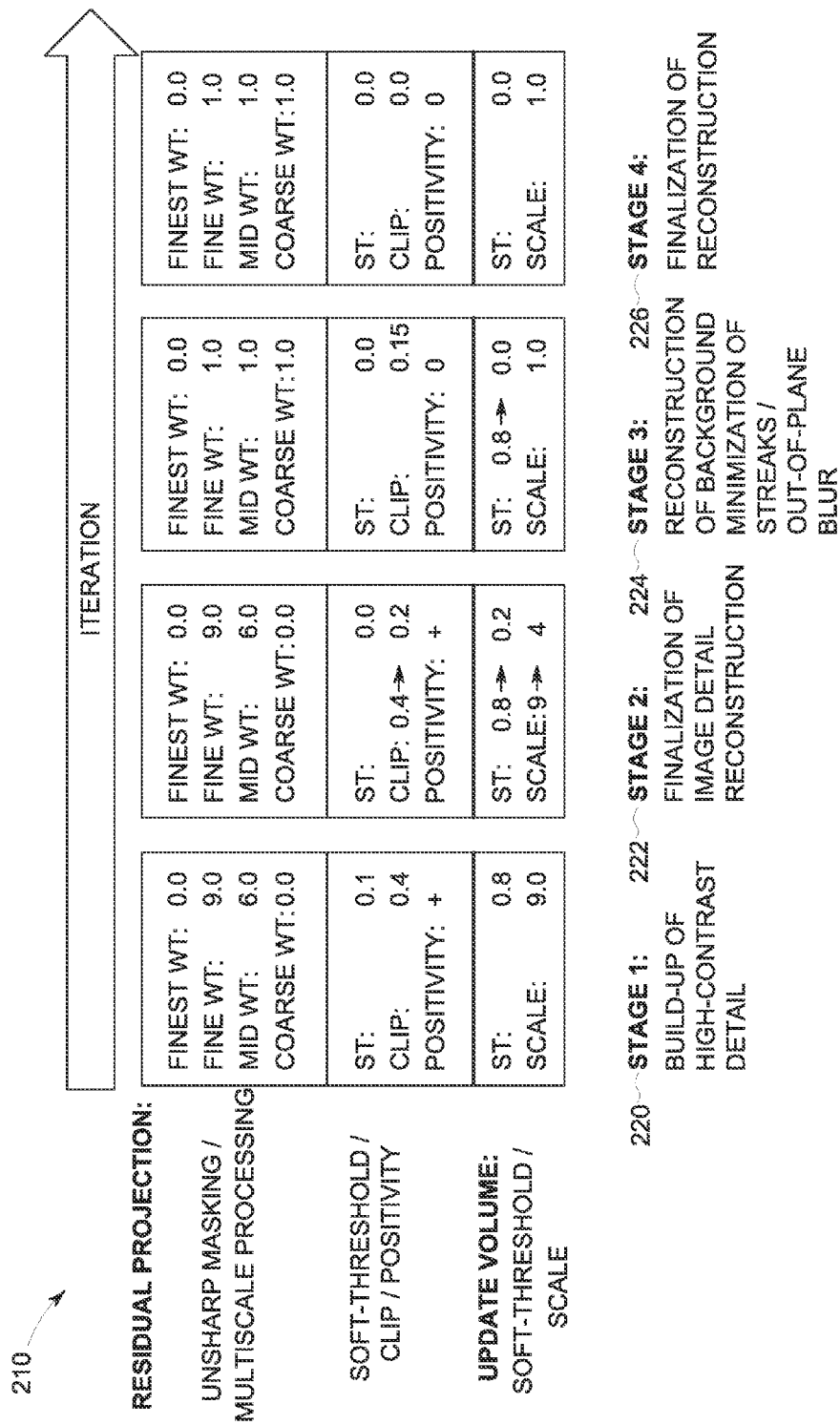
FIG. 5 depicts a parameter schedule for an iterative reconstruction process, in accordance with aspects of the present disclosure.

Per the depicted schedule 210 of FIG. 5, four distinct stages of the multi-stage iterative reconstruction process are shown. Stage 1 is directed to building up high-contrast fine-scale detail (e.g., contrast enhanced blood vessels). Stage 2 is directed to finalizing the reconstruction of this high-contrast detail, while also progressing to lower contrast fine-scale detail. Note that both Stage 1 and Stage 2 are directed toward reconstructing fine-scale detail, while Stage 3 is directed to reconstructing the background with minimization of streak artifacts and out-of-plane blur. Lastly, stage 4 is directed to finalizing the reconstruction. In addition, in this example, four image scales (i.e., finest, fine, mid, and coarse) are utilized with respect to the decomposition of the residual projection images 154 in the multi-scale or frequency band processing. As will be appreciated, in other implementations, more (e.g., five, six, seven, and so forth) or less (e.g., two or three) image scales may be utilized in the decomposition step. Also, as discussed earlier, no discrete image scales or frequency bands may be identified, and a similar processing may be implemented, for example, that acts on a continuous frequency scale. Further, as noted above, the number of image scales or frequency bands may also change during the iterative process. For example, three image scales or frequency bands (e.g., fine, mid, coarse) may be employed for certain of the stages, while four image scales or frequency bands (e.g., finest, fine, mid, coarse) may be employed for others. In addition, the method or basis for decomposition of the residual projections 154 may change for different stages. For example, some stages may decompose the residual projections 154 into frequency bands or based upon frequency criteria, while other stages may decompose the residual projections 154 based on image scales or similar criteria.

With this in mind, and turning back to FIG. 5, Stage 1 is now described. In this stage, which is directed to the build-up of high contrast detail, a main component of the frequency-band (or multi-scale) processing is the suppression of the background in the residual projection images (i.e., the associated weight is set to zero, or a small value). The remaining parts of the filter weights reflect a ramp characteristics (i.e., relatively higher weight for fine-scale detail) in combination with noise-suppression (i.e., finest scale may be set to zero, or may receive a relatively small weight).

The frequency band processing is followed by a clipping in order to equilibrate the contribution of the detail image to the reconstructed volume, thus facilitating the management of streak artifacts after the backprojection step. The clipping of the residual projection images may be combined with a soft-thresholding in order to address remaining image noise, and more generally suppress low intensity image content (i.e., selectively emphasize higher contrast structures in the image over low contrast structures), as well as applying a positivity constraint to the images that preserves only detail that has higher (i.e., positive) contrast relative to the respective background.

As noted above, the modified residual projection images 168 are backprojected, and the resulting image volume is soft-thresholded in order to minimize streaks and build up only the detail structures in the imaged volume. In order to counter-act the reduction of contrast in the image update volume 182 as well as the small spatial extent of the reconstructed image content, a scale factor is applied, and the image update volume 182 is added (step 190) to the existing estimate 192 of the volume.

An implementation of a parameter schedule corresponding to this approach is shown in FIG. 5 in the column pertaining to Stage 1. As shown, the parameters characterizing the multi-scale processing part correspond to the respective weights (e.g., Finest Wt, Fine Wt, and so forth) when the different image scales are re-assembled into a single image within the multi-scale or frequency band processing step. Note that the general characteristic corresponds to a ramp-type filter, with the low-frequency component set to zero (to remove coarse scale background), along with the finest scale component (for noise suppression). The soft-threshold and clipping parameters (i.e., 0.1 and 0.4 respectively, as shown in FIG. 5) for additional processing of the filtered images (FIG. 4, step 164) are defined relative to a reference value derived from the (processed) projection images (or residuals). In particular, in one embodiment the reference value is the mini-max of those images (i.e., the minimum of the set consisting of the maximum values of all projection images—where the maximum may be chosen relative to an ROI that excludes the periphery of the images). A soft-thresholding parameter of 0.1, and a clipping parameter of 0.4 means that the values between 0.1 and 0.4 times the reference value are retained. That is, all values with an absolute value larger than 0.4 times the reference value are clipped, the remaining part of the signal is soft-thresholded, with a threshold value of 0.1 times the reference value. In addition, a positivity constraint is applied, therefore rejecting all negative values in the image, and therefore minimizing the impact of any negative undershoot effects due to the high-pass filtering characteristic near high-contrast edges in the image. (The resulting images after the additional processing 164 represent the modified projection images 168). After the backprojection of the modified projection images 168, the resulting image is soft-thresholded, where the controlling parameter (i.e., 0.8) is defined similarly as before, but now relative to the maximum value in the backprojected image (where the maximum may be taken with respect to a ROI near the center of the imaged volume). Note that the reference values (used to determine the thresholds, e.g., for soft thresholding and clipping) for each iterative update may be determined based on the most recent (residual) projection, or backprojected data, respectively; or they may be selected at the beginning of the current stage of the reconstruction and held fixed throughout the current stage, or they may be selected at the start of the reconstruction, and held fixed throughout the reconstruction process. Hybrid strategies may also be used. Different strategies to selecting the reference parameters may be used for different elements in the process.

The last step in each stage is a scaling of the update volume. This scale factor is selected to counteract the loss in contrast due to the soft thresholding in the reconstruction domain, as well as the soft thresholding and clipping in the projection domain. This scale factor also ensures faster convergence of the reconstruction method, but is selected such as to avoid "overcompensating", i.e., such that the true contrast of a small structure is approached "from below" throughout the iterative process.

The first stage of the reconstruction process is generally focused on building up small, high-contrast structures that are for the most part included in the finer image scales corresponding to (small) image detail, while also minimizing the introduction of streak artifacts due to those structures. Due to the combination of clipping/soft-thresholding (in the projection domain) and the soft-thresholding (after the backprojection) there may be residual fine detail content in the images after the first stage. This residual fine detail content is of lower contrast (since most of the corresponding image structures are already partially reconstructed), but may still cause streak artifacts and have an undesirable impact on the background. Therefore, in Stage 2, the frequency band processing is left essentially unchanged, but more of the detail image content is incorporated into the reconstruction by gradually lowering the clipping threshold in the projection domain and also lowering the soft-threshold value in the backprojected domain. Correspondingly, the factor that is used to scale the image update before adding to the current estimate of the image is also gradually lowered.

With reference to the example shown in FIG. 5, examples of parameter values and, in some instances, changes to these parameters are shown for one such implementation. In this example, the soft-thresholding parameter in the image domain is incrementally lowered during this stage, reflecting a less aggressive strategy in suppressing streak artifacts, while the scale factor is also lowered correspondingly. In one implementation, in order to ensure that this parameter does in fact decrease, the corresponding reference value is not determined independently at each iteration, but the reference value from the first iteration step in this stage is used throughout this stage.

In Stage 3, the background is reconstructed with a minimization of streaks artifacts and out-of-plane blur. In this stage, the background image, which generally corresponds to lower frequency image content is built up. In this example, the frequency-band processing is set up such as to essentially maintain the image as is (i.e., weights of 1.0 for most image scales or frequency bands), perhaps in combination with a suppression (i.e., weight of 0) of the finest scales which may reflect noise content in the images. However, in order to minimize streaks in the reconstructed volume (now due to lower frequency image content, perhaps at intermediate scales), clipping may be applied in the projection domain, as well as soft-thresholding in the backprojected volume domain. For similar reasons as described above, the soft-thresholding parameter may be relaxed over time (i.e., decreased).

Turning to FIG. 5, in the depicted example at Stage 3 the weights for all scales of the projection image are now set to 1.0 (with the exception of the finest scale, which is kept at 0.0 in order to manage image noise). Since the goal of this stage is generally on reconstruction of the (low-frequency) background, the background low-frequency image content is preserved, and the detail image content is not enhanced. In order to allow for a gradual build-up of the background, clipping of the projection images is performed and the scale factor applied to the backprojected (and soft-thresholded) image is set to 1.0. The soft-threshold parameter for the backprojected volume is decreasing from 0.8 (aggressive) to 0 (no soft-thresholding), thereby reducing the artifact reduction impact over time, and transitioning more to a "simple backprojection" type update characteristic. In this example, the reference value for the clipping of the projection images is set at a fixed value for the whole stage in the first iteration of this stage (as in the previous stage), thereby making sure that the clipping value is in fact constant.

Note that the discussed schedule as described in this example is suited for updates where the background is initialized with a reasonably uniform gray scale setting. This is due to the fact that with a "zero" initialization of the background the initial update steps will consists mostly of uniform updates of the reconstructed volume (as a consequence of the clipping in the projection image domain); the applied soft-thresholding step will merely reduce the background intensity to a lower uniform value, and therefore temporarily slow the convergence. Once a sufficient intensity of the background is achieved, however, the soft-thresholding and so forth will become once more effective. Appropriate initialization of the background, e.g., with an appropriate uniform value (which is achieved by—at the appropriate iteration step-adding a constant value to the current estimate of the volume, maybe constrained to the known or estimated support of the object), is straightforward and within the scope of the current invention.

At Stage 4, the reconstruction is finalized. In one example, the iteration steps in this final stage correspond to a simple Simultaneous Algebraic Reconstruction Technique (SART)-type update. In such an implementation, there is no frequency band processing of the residual images (with the possible exception of noise suppression by assigning a small weight to the finest scale), and there is no clipping/soft-thresholding applied at either the projection image level, or at the level of the backprojected volume.

The parameter schedule in this final stage (as shown in FIG. 5) reflects a simple backprojection update, with no clipping or soft-thresholding at any stage in the process. In this manner, any existing residual signal may be cleaned up and some degree of reprojection consistency enforced. Ideally, the residual images 154 are already zero uniformly when going into this stage, and this stage will do very little to change the existing estimate 192 of the imaged volume.

As will be appreciated, the present description is intended to provide explanation of the present approach in an accessible format and, thus, discrete and separate steps are describes where, in practice an integrated approach may be employed. For example, all smoothing and weighting of different bands or scales may be consolidated into a single digital filter or filter operation. Similarly, Nesterov-type updates may be employed, effectively combining updates from more than a single step (i.e., iteration) in order to derive updates for faster convergence. Also, the reconstruction steps as described here encourage a "sparse" representation of the reconstructed volume. Explicit steps may be incorporated into the reconstruction approach of the current invention that minimize/improve a mathematically formulated sparseness criterion (e.g., TV—total variaton, or other suitable criteria). Further, data may be segregated or binned for more efficient processing. For example, background and detail data may be kept as separate volumes and combined using a weighted combination for visualization. Such an approach may allow for the use of even more scales. Note that in one embodiment, for example, in Stages 3 and 4 the scaling factor for all but the coarsest scale(s) are set to zero. In this way, these stages reconstruct only the coarse scale background, but do not update the fine-scale structure of the reconstruction images (although still acting on the same volume that already contains the fine-scale structure as build up from Stages 1 and 2). In yet another embodiment, two or more volumes are created in parallel, e.g., one containing the fine-scale detail, the other containing the coarse scale background, where residual projection images at some stage of the process may be created by reprojecting the sum of both volumes.

Technical effects of the invention include generating a volumetric representation using an iterative reconstruction where part of the iterative reconstruction involves decomposing a projection image into different scales or frequency bands at each step and differentially processing the respective decomposed projection images.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An iterative image reconstruction method, comprising:
   accessing a set of projection images;
   performing a first stage of a multi-stage iterative reconstruction of the set of projection images, each stage comprising one or more iterative steps, wherein each iterative step comprises:
      creating modified projection images;
      backprojecting the modified projection images to create an image volume update in image space for a current image volume estimate;
      creating a modified image volume update for the current iterative step;
      adding the modified image volume update to the current image volume estimate to form an updated image volume estimate; and
      reprojecting the updated image volume estimate to create residual projection images in projection space for use in the next iterative step; wherein the first stage selectively emphasizes a subset of features of the projection images for iterative processing, wherein the selective emphasis of the first stage is defined by one or more parameters specified for the first stage;
   subsequent to the first stage, performing at least a second stage of the multi-stage iterative reconstruction, wherein the second stage selectively emphasizes a different subset of features of the projection images for iterative processing, wherein the selective emphasis of the second stage is defined by one or more parameters specified for the second stage that differ in value or range from the first stage; and
   upon satisfying a completion criterion, concluding the multi-stage iterative reconstruction and generating a final image.

2. The method of claim 1, wherein the selective emphasis of one or both of the first stage or second stage is selective with respect to structure size or scale within the set of projection images.

3. The method of claim 1, wherein the selective emphasis of one or both of the first stage or second stage is selective with respect to structure contrast within the set of projection images.

4. The method of claim 1, wherein the selective emphasis is applied in the projection domain by selecting at least one of image scale or contrast.

5. The method of claim 1, wherein the selective emphasis comprises utilizing artifact management in a backprojected volume.

6. The method of claim 1, further comprising performing a transition stage between the first stage and the second stage, wherein the transition stage comprises a transition between the selective emphasis of the first stage and the second stage and is associated with transitional values of the one or more parameters.

7. The method of claim 6, wherein the transition stage comprises applying less selective emphasis relative to the preceding stage.

8. An iterative image reconstruction method, comprising:
   accessing a set of projection images;
   performing an iterative reconstruction comprising two or more stages, each stage comprising a plurality of iterative steps, wherein each iterative step comprises:
      creating modified projection images;

backprojecting the modified projection images to create an image volume update in image space for a current image volume estimate;
creating a modified image volume update for the current iterative step;
adding the modified image volume update to the current image volume estimate to form an updated image volume estimate; and
reprojecting the updated image volume estimate to create residual projection images in projection space for use in the next iterative step; wherein at least one stage of the iterative reconstruction selectively emphasizes, relative to other stages, a subset of features of the projection images for iterative processing by applying one or more of selective weighting, thresholding, or clipping based on parameters specified for the respective stage; and
upon satisfying a completion criterion, concluding the iterative reconstruction and generating a final image.

9. The method of claim 8, wherein one or more additional stages of the reconstruction method selectively emphasizes a different subset of features, relative to other stages, by applying one or more of selective weighting, thresholding, or clipping based on different parameters specified for the respective stage.

10. The method of claim 8, wherein each of the two or more stages is directed to selectively emphasizing a different aspect of image quality of the final image.

11. The method of claim 8, wherein at least one stage of the reconstruction method selectively emphasizes fine structure within the image and another stage emphasizes background structure.

12. The method of claim 8, comprising accessing a parameter schedule specifying the parameters for each stage of the iterative reconstruction.

13. The method of claim 8, wherein, within at least one stage, each iterative step decomposes an input projection image into two or more decomposition images based on image scale or frequency band.

14. The method of claim 13, wherein the two or more decomposition images are differentially weighted to achieve the selective emphasis of the subset of features within the respective stage.

15. An image reconstruction system, comprising:
a display;
a memory or storage component storing one or more routines; and
a processing component configured to execute the one or more routines, wherein the one or more routines, when executed by the processing component, cause acts to be performed comprising:
accessing a set of projection images;
performing a first stage of a multi-stage iterative reconstruction of the set of projection images, each stage comprising one or more iterative steps, wherein each iterative step comprises:
creating modified projection images;
backprojecting the modified projection images to create an image volume update in image space for a current image volume estimate;
creating a modified image volume update for the current iterative step;
adding the modified image volume update to the current image volume estimate to form an updated image volume estimate;
reprojecting the updated image volume estimate to create residual projection images in projection space for use in the next iterative step;
wherein the first stage selectively emphasizes a subset of features of the projection images for iterative processing, wherein the selective emphasis of the first stage is defined by one or more parameters specified for the first stage;
subsequent to the first stage, performing at least a second stage of the multi-stage iterative reconstruction, wherein the second stage selectively emphasizes a different subset of features of the projection images for iterative processing, wherein the selective emphasis of the second stage is defined by one or more parameters specified for the second stage that differ in value or range from the first stage; and
upon satisfying a completion criterion, concluding the multi-stage iterative reconstruction and generating a final image.

16. The image reconstruction system of claim 15, wherein the selective emphasis of one or both of the first stage or second stage is selective with respect to structure size or scale within the set of projection images.

17. The image reconstruction system of claim 15, wherein the selective emphasis of one or both of the first stage or second stage is selective with respect to structure contrast within the set of projection images.

18. The image reconstruction system of claim 15, wherein the selective emphasis is applied in the projection domain by selecting at least one of image scale or contrast.

19. The image reconstruction system of claim 15, wherein the selective emphasis comprises utilizing artifact management in a backprojected volume.

20. The image reconstruction system of claim 15, wherein at least one stage of the multi-stage iterative reconstruction selectively emphasizes fine structure within the image and another stage emphasizes background structure.

* * * * *